United States Patent
Ali et al.

(10) Patent No.: US 6,606,511 B1
(45) Date of Patent: Aug. 12, 2003

(54) PULSE OXIMETRY PULSE INDICATOR

(75) Inventors: Ammar Al Ali, Tustin, CA (US); Divya S. Breed, Laguna Niguel, CA (US); Jerome J. Novak, Aliso Viejo, CA (US)

(73) Assignee: Masimo Corporation, Irvine, CA (US)

(*) Notice: Subject to any disclaimer, the term of this patent is extended or adjusted under 35 U.S.C. 154(b) by 0 days.

(21) Appl. No.: 09/478,230

(22) Filed: Jan. 6, 2000

Related U.S. Application Data

(60) Provisional application No. 60/115,289, filed on Jan. 7, 1999.

(51) Int. Cl.$^7$ .............................................. A61B 5/00
(52) U.S. Cl. .................................... 600/324; 600/323
(58) Field of Search ............................. 600/309–310, 600/322–324, 330, 336, 508, 515–519

(56) References Cited

U.S. PATENT DOCUMENTS

| | | | |
|---|---|---|---|
| 3,875,930 A | | 4/1975 | Silva et al. |
| 4,193,393 A | | 3/1980 | Schlager |
| 4,222,044 A | | 9/1980 | Boschung |
| 4,694,200 A | | 9/1987 | Hetyei |
| 4,714,341 A | * | 12/1987 | Hamaguri et al. ............ 356/41 |
| 4,739,766 A | * | 4/1988 | Riederer .................... 600/413 |
| 4,800,495 A | * | 1/1989 | Smith ........................ 600/322 |
| 4,863,265 A | * | 9/1989 | Flower et al. ................ 356/41 |
| 5,031,629 A | * | 7/1991 | DeMarzo .................... 600/483 |
| 5,090,418 A | * | 2/1992 | Squires et al. .............. 600/515 |
| 5,199,048 A | | 3/1993 | Wakabayashi |
| 5,299,120 A | * | 3/1994 | Kaestle ....................... 600/310 |
| 5,372,134 A | | 12/1994 | Richardson |
| 5,517,988 A | * | 5/1996 | Gerhard ...................... 600/323 |
| 5,751,911 A | * | 5/1998 | Goldman ..................... 706/20 |
| 5,810,740 A | * | 9/1998 | Paisner ....................... 600/515 |
| 5,819,007 A | * | 10/1998 | Elghazzawi ................. 706/46 |
| 5,865,736 A | * | 2/1999 | Baker, Jr. et al. ........... 600/323 |
| 5,944,669 A | * | 8/1999 | Kaib .......................... 600/512 |
| 5,967,994 A | * | 10/1999 | Wang .......................... 600/509 |
| 6,002,952 A | | 12/1999 | Diab et al. |
| 6,083,172 A | * | 7/2000 | Baker, Jr. et al. ........... 600/500 |
| 6,122,535 A | * | 9/2000 | Kaestle et al. ............. 600/322 |
| 6,339,715 B1 | | 1/2002 | Bahr et al. |

FOREIGN PATENT DOCUMENTS

| | | |
|---|---|---|
| DE | 3723566 | 1/1989 |
| EP | 617912 | 10/1994 |
| EP | 813102 | 5/1997 |
| WO | WO 98/43071 | 10/1998 |
| WO | WO 00/38569 | 7/2000 |
| WO | WO 00/40147 | 7/2000 |
| WO | WO 00/56209 | 9/2000 |
| WO | WO 00/61000 | 10/2000 |

OTHER PUBLICATIONS

Webster's II New Riverside University Dictionary, Riverside Publishing Company, 1994, p. 903.*

* cited by examiner

*Primary Examiner*—Eric F. Winakur
*Assistant Examiner*—Matthew Kremer
(74) *Attorney, Agent, or Firm*—Knobbe, Martens, Olson & Bear LLP

(57) ABSTRACT

An intelligent, rule-based processor provides a pulse indicator designating the occurrence of each pulse in a pulse oximeter-derived photo-plethysmograph waveform. When there is relatively no distortion corrupting the plethysmograph signal, the processor analyzes the shape of the pulses in the waveform to determine where in the waveform to generate the pulse indication. When distortion is present, looser waveform criteria are used to determine if pulses are present. If pulses are present, the pulse indication is based upon an averaged pulse rate. If no pulses are present, no indication occurs. The pulse indicator provides a trigger and amplitude output. The trigger output is used to initiate an audible tone "beep" or a visual pulse indication on a display, such as a vertical spike on a horizontal trace or a corresponding indication on a bar display. The amplitude output is used to indicate data integrity and corresponding confidence in the computed values of saturation and pulse rate. The amplitude output can vary a characteristic of the pulse indicator, such as beep volume or frequency or the height of the visual display spike.

11 Claims, 16 Drawing Sheets

PULSE OXIMETRY PULSE INDICATOR

This application relates to and claims the benefit of priority to U.S. Provisional Application Ser. No. 60/115,289 filed Jan. 7, 1999.

BACKGROUND OF THE INVENTION

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximeter typically provides a numerical readout of the patient's oxygen saturation, a numerical readout of pulse rate, and an audible indicator or "beep" that occurs in response to each pulse. In addition, a pulse oximeter may display the patient's plethysmograph waveform, which is a visualization of blood volume change in the illuminated tissue caused by pulsatile arterial blood flow over time. The plethysmograph provides a visual display that is also indicative of the patient's pulse and pulse rate.

A pulse oximetry system consists of a sensor attached to a patient, a monitor, and a cable connecting the sensor and monitor. Conventionally, a pulse oximetry sensor has both red and infrared (IR) light-emitting diode (LED) emitters and a photodiode detector. The sensor is typically attached to a patient's finger or toe, or a very young patient's patient's foot. For a finger, the sensor is configured so that the emitters project light through the fingernail and into the blood vessels and capillaries underneath. The photodiode is positioned at the fingertip opposite the fingernail so as to detect the LED transmitted light as it emerges from the finger tissues.

The pulse oximetry monitor (pulse oximeter) determines oxygen saturation by computing the differential absorption by arterial blood of the two wavelengths emitted by the sensor. The pulse oximeter alternately activates the sensor LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the sensor, processing the sensor signals and displaying the patient's oxygen saturation and pulse rate. A pulse oximeter is described in U.S. Pat. No. 5,632,272 assigned to the assignee of the present invention.

SUMMARY OF THE INVENTION

FIG. 1 illustrates the standard plethysmograph waveform 100, which can be derived from a pulse oximeter. The waveform 100 is a display of blood volume, shown along the y-axis 110, over time, shown along the x-axis 120. The shape of the plethysmograph waveform 100 is a function of physiological conditions including heart stroke volume, pressure gradient, arterial elasticity and peripheral resistance. The ideal waveform 100 displays a broad peripheral flow curve, with a short, steep inflow phase 130 followed by a 3 to 4 times longer outflow phase 140. The inflow phase 130 is the result of tissue distention by the rapid blood volume inflow during ventricular systole. During the outflow phase 140, blood flow continues into the vascular bed during diastole. The end diastolic baseline 150 indicates the minimum basal tissue perfusion. During the outflow phase 140 is a dicrotic notch 160, the nature of which is disputed. Classically, the dicrotic notch 160 is attributed to closure of the aortic valve at the end of ventricular systole. However, it may also be the result of reflection from the periphery of an initial, fast propagating, pressure pulse that occurs upon the opening of the aortic valve and that precedes the arterial flow wave. A double dicrotic notch can sometimes be observed, although its explanation is obscure, possibly the result of reflections reaching the sensor at different times.

FIGS. 2–3B illustrate plethysmograph waveforms 200, 310, 360 that display various anomalies. In FIG. 2, the waveform 200 displays two arrhythmias 210, 220. In FIG. 3A, the waveform 310 illustrates distortion corrupting a conventional plethysmograph 100 (FIG. 1). FIG. 3B shows a filtered waveform 360 after distortion has been removed through adaptive filtering, such as described in U.S. Pat. No. 5,632,272 cited above. FIG. 3B illustrates that, although the waveform 360 is filtered, the resulting pulses 362 have shapes that are distorted in comparison to the pulses illustrated in FIG. 1.

A desirable feature of pulse oximeters is an audible "beep" tone produced to correspond to the patient's pulse. Conventionally, the beep is triggered from recognition of some aspect of the plethysmograph waveform shape. Such a waveform-triggered beep may indicate an arrhythmia, like those displayed in FIG. 2, but may also generate false pulse indications as the result of motion-artifact or noise induced waveform distortion, as illustrated in FIGS. 3A and 3B. This characteristic results because both distortion and arrhythmias result in anomalies in the plethysmograph waveform shape on which this beep mechanism is dependent. Alternatively, the beep can be triggered from a time base set to the average pulse rate. Signal processing can generate an average pulse rate that is resistant to distortion induced error. A pulse beep based on average pulse rate is relatively insensitive to episodes of distortion, but is likewise insensitive to arrhythmias.

An example of the determination of pulse rate in the presence of distortion is described in U.S. patent application Ser. No. 08/834,194, filed Apr. 14, 1997 (now U.S. Pat. No. 6,002,952), entitled "Improved Signal Processing Apparatus and Method," which is assigned to the assignee of the current application and incorporated by reference herein. Another example of pulse rate determination in the presence of distortion is described in U.S. Pat. No. 6,463,311, entitled "Plethysmograph Pulse Recognition Processor," which is assigned to the assignee of the current application and incorporated by reference herein.

One aspect of the present invention is a processor having a decision element that determines if the waveform has little or no distortion or significant distortion. If there is little distortion, the decision element provides a trigger in real-time with physiologically acceptable pulses recognized by a waveform analyzer. If there is significant distortion, then the decision element provides the trigger based synchronized to an averaged pulse rate, provided waveform pulses are detected. The trigger can be used to generate an audible pulse beep that is insensitive to episodes of significant distortion, but is capable of responding to arrhythmia events.

Another desirable feature for pulse oximeters is a visual indication of the patient's pulse. Conventionally, this is provided by an amplitude-versus-time display of the plethysmograph waveform, such as illustrated in FIG. 1. Some monitors are only capable of a light-bar display of the plethysmograph amplitude. Regardless, both types of displays provide a sufficient indication of the patient's pulse only when there is relatively small distortion of the plethysmograph waveform. When there is significant distortion, such as illustrated in FIG. 3A, the display provides practically no information regarding the patient's pulse.

Yet another desirable feature for pulse oximeters is an indication of confidence in the input data. Conventionally, a visual display of a plethysmograph waveform that shows relatively small distortion would convey a high confidence level in the input data and a corresponding high confidence in the saturation and pulse rate outputs of the pulse oximeter. However, a distorted waveform does not necessarily indicate low confidence in the input data and resulting saturation and pulse rate outputs, especially if the pulse oximeter is designed to function in the presence of motion-artifact.

Another aspect of the current invention is the generation of a data integrity indicator that is used in conjunction with the decision element trigger referenced above to create a visual pulse indicator. The visual pulse indicator is an amplitude-versus-time display that can be provided in conjunction with the plethysmograph waveform display. The trigger is used to generate a amplitude spike synchronous to a plethysmograph pulse. The data integrity indicator varies the amplitude of the spike in proportion to confidence in the measured values.

Yet another aspect of the present invention is a processing apparatus that has as an input a plethysmograph waveform containing a plurality of pulses. The processor generates a trigger synchronous with the occurrence of the pulses. The processor includes a waveform analyzer having the waveform as an input and responsive to the shape of the pulses. The processor also includes a decision element responsive to the waveform analyzer output when the waveform is substantially undistorted and responsive to pulse rate when the waveform is substantially distorted. The trigger can be used to generate an audible or visual indicator of pulse occurrence. A measure of data integrity can also be used to vary the audible or visual indicators to provide a simultaneous indication of confidence in measured values, such as oxygen saturation and pulse rate.

A further aspect of the current invention is a method of indicating a pulse in a plethysmograph waveform. The method includes the steps of deriving a measure of distortion in the waveform, establishing a trigger criterion dependent on that measure, determining whether the trigger criterion is satisfied to provide a trigger, and generating a pulse indication upon occurrence of the trigger. The deriving step includes the sub-steps of computing a first value related to the waveform integrity, computing a second value related to the recognizable pulses in the waveform, and combining the first and second values to derive the distortion measure. The trigger criterion is based on waveform shape and possibly on an averaged pulse rate.

One more aspect of the current invention is an apparatus for indicating the occurrence of pulses in a plethysmograph waveform. This apparatus includes a waveform analyzer means for recognizing a physiological pulse in the waveform. Also included is a detector means for determining a measure of distortion in the waveform and a decision means for triggering an audible or visual pulse indicator. The decision means is based the physiological pulse and possibly the pulse rate, depending on the distortion measure.

DETAILED DESCRIPTION OF THE PREFERRED EMBODIMENTS

Figure 1:
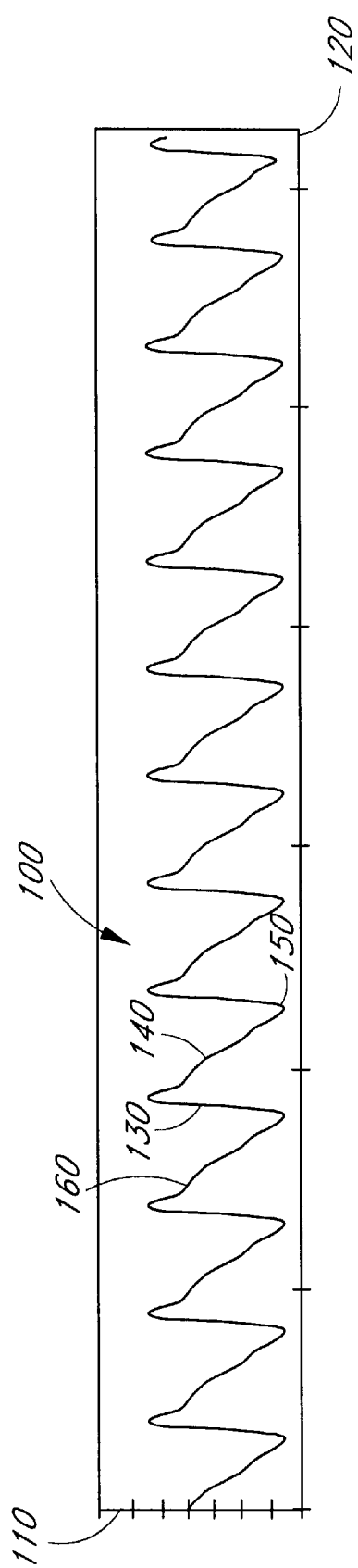
FIG. 1 illustrates a standard plethysmograph waveform that can be derived from a pulse oximeter.
Figure 2:
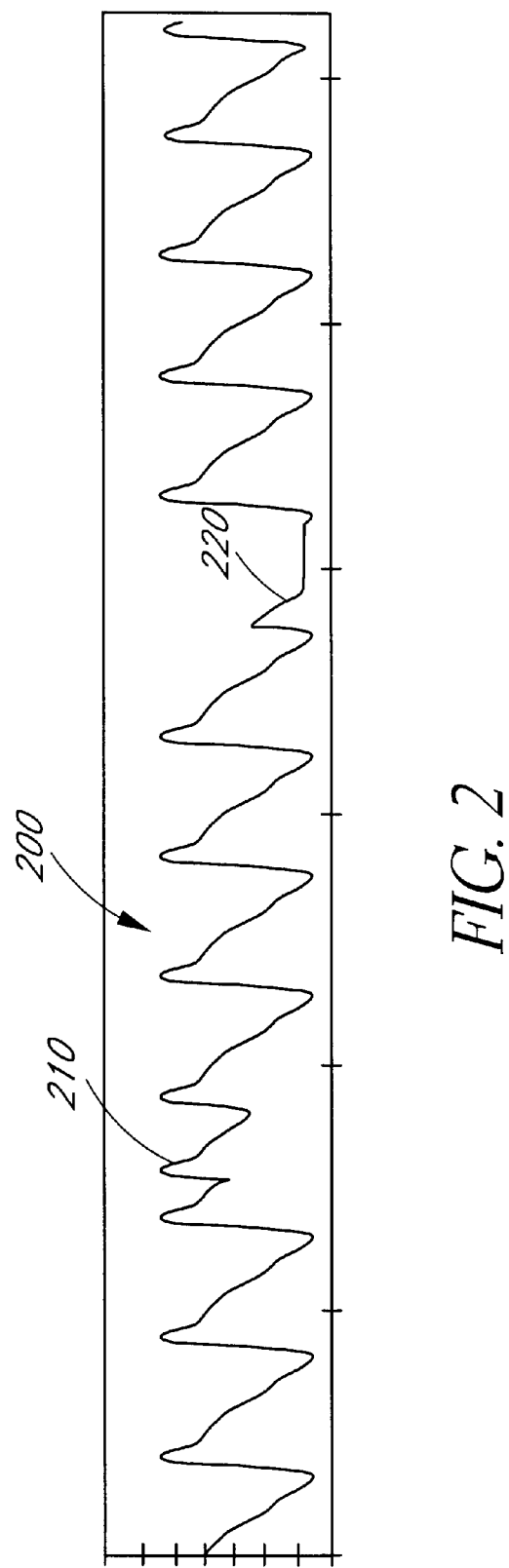
FIG. 2 illustrates a plethysmograph waveform showing an arrhythmia.
Figure 3A:
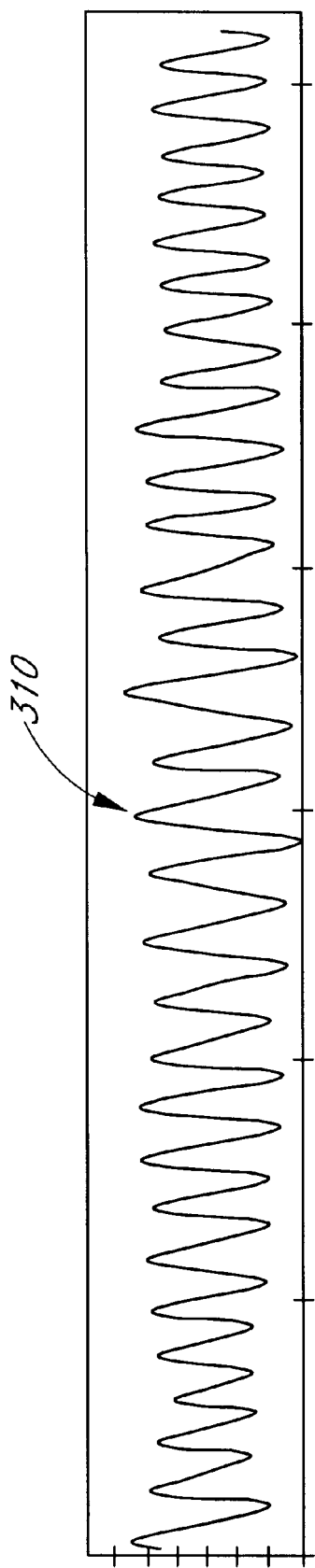
FIG. 3A illustrates a plethysmograph waveform corrupted by distortion.
Figure 3B:
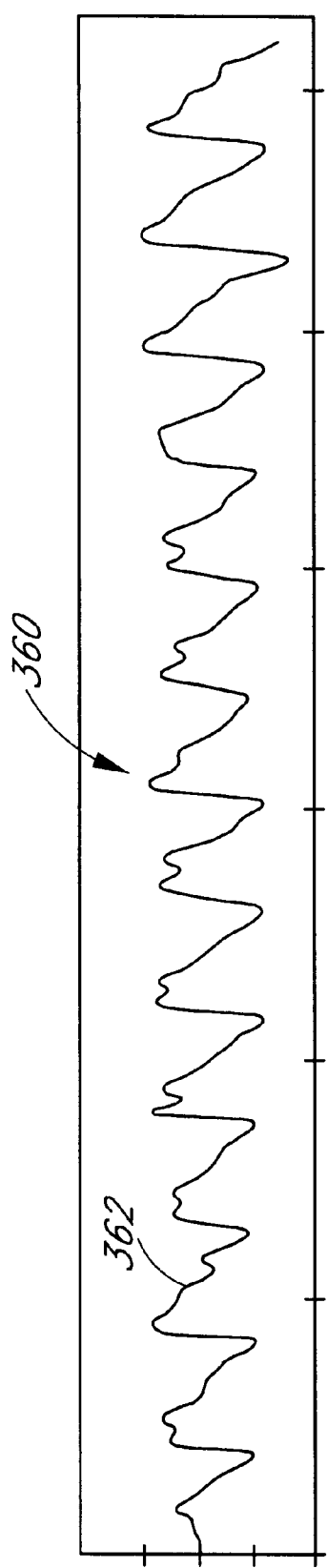
FIG. 3B illustrates a filtered plethysmograph corresponding to the distortion-corrupted plethysmograph of FIG. 3A.
Figure 4:
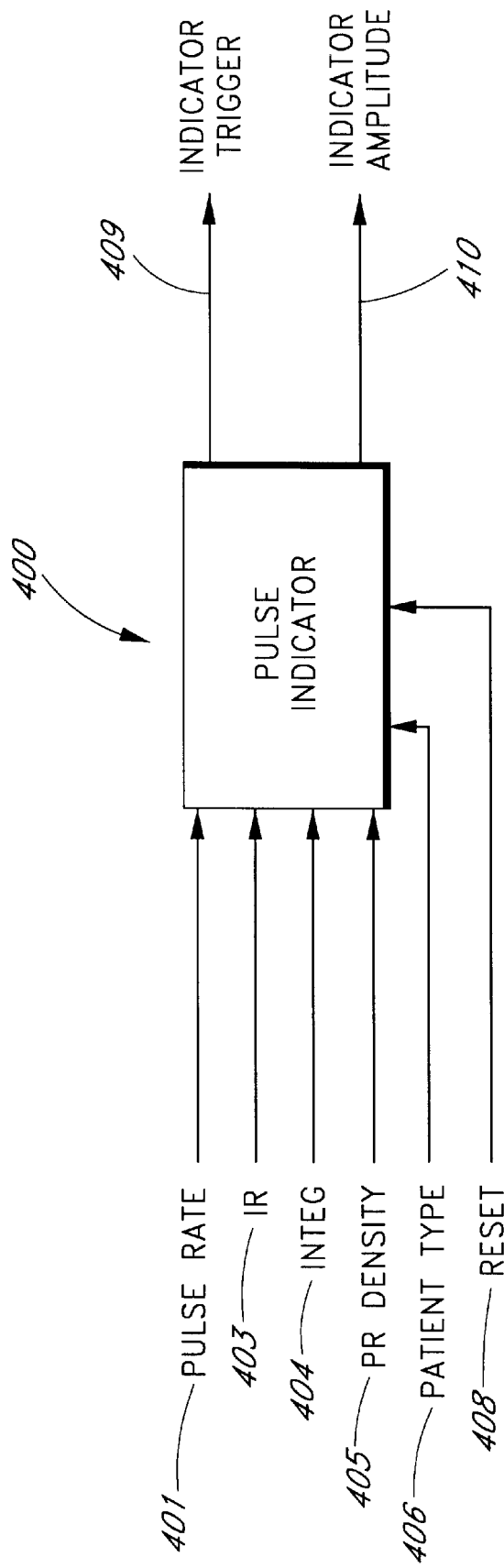
FIG. 4 illustrates the inputs and outputs of the pulse indicator according to the present invention.

FIG. 4 illustrates a pulse indicator 400, which can be incorporated into a pulse oximeter to trigger the occurrence of a synchronous indication of each of the patient's arterial pulses. The indicator 400 operates on an IR signal input 403 and generates a trigger output 409 and an amplitude output 410. The trigger output 409 can be connected to a tone generator within the pulse oximeter monitor to create a fixed-duration audible "beep" as a pulse indication. Alternatively, or in addition, the trigger output can be connected to a display generator within the pulse oximeter monitor to create a visual pulse indication. The visual pulse indication can be a continuous horizontal trace on a CRT, LCD display or similar display device, where vertical spikes occur in the trace synchronously with the patient's pulse, as described in more detail below. Alternatively, the visual pulse indication can be a bar display, such as a vertically- or horizontally-arranged stack of LEDs or similar display device, where the bar pulses synchronously with the patient's pulse.

The amplitude output 410 is used to vary the audible or visual indications so as to designate input data integrity and a corresponding confidence in the saturation and pulse rate outputs of the pulse oximeter. For example, the height of the vertical spike can be varied in proportion to the amplitude output 410, where a large or small vertical spike would correspondingly designate high or low confidence. As another example, the amplitude output 410 can be used to vary the volume of the audible beep or to change the visual indication (e.g., change color or the like) to similarly designate a high or low confidence. One of ordinary skill in the art will recognize that the trigger output 409 and amplitude output 410 can be utilized to generate a variety of audible and visual indications of a patient's pulse and data integrity within the scope of this invention.

Other inputs to the pulse indicator 400 include pulse rate 401, Integ 404, PR density 405, patient type 406 and reset 408, which are described in detail below. The beep decision involves a rule-based process that advantageously responds to the pulse waveforms of the patient's plethysmograph in low-noise or no-distortion situations, but becomes dependent an averaged pulse rate during high-noise or distortion situations. This "intelligent beep" reliably indicates the patient's pulse, yet responds to patient arrhythmias, asystole conditions and similar irregular plethysmographs.

The pulse rate input 401 to the pulse indicator 400 provides the frequency of the patient's pulse rate in beats per minute. Pulse rate can be determined as described in U.S. patent application Ser. No. 08/834,194 or U.S. Patent Application entitled "Plethysmograph Pulse Recognition Processor," both cited above.

Figure 5A:
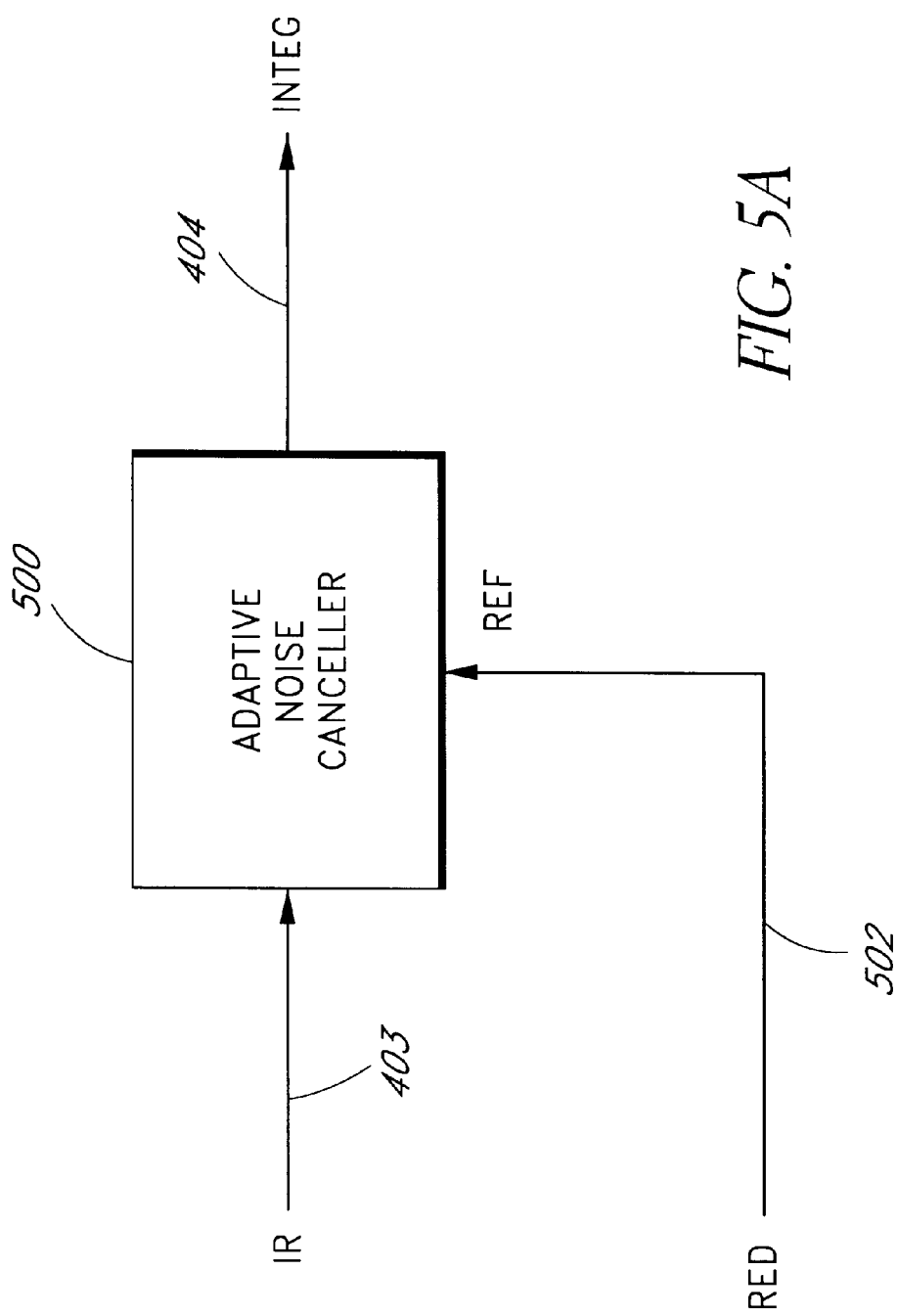
FIG. 5 illustrates the generation of one of the pulse indicator inputs.

FIG. 5A illustrates the generation of the Integ input 404 to the pulse indicator 400 (FIG. 4). The IR 403 and Red 502 signals derived from a pulse oximetry sensor are input to an adaptive noise canceller 500 having Integ 404 as an output. The Integ output 404 is a measure of the integrity of the IR 403 and Red 502 input signals.

Figure 5B:
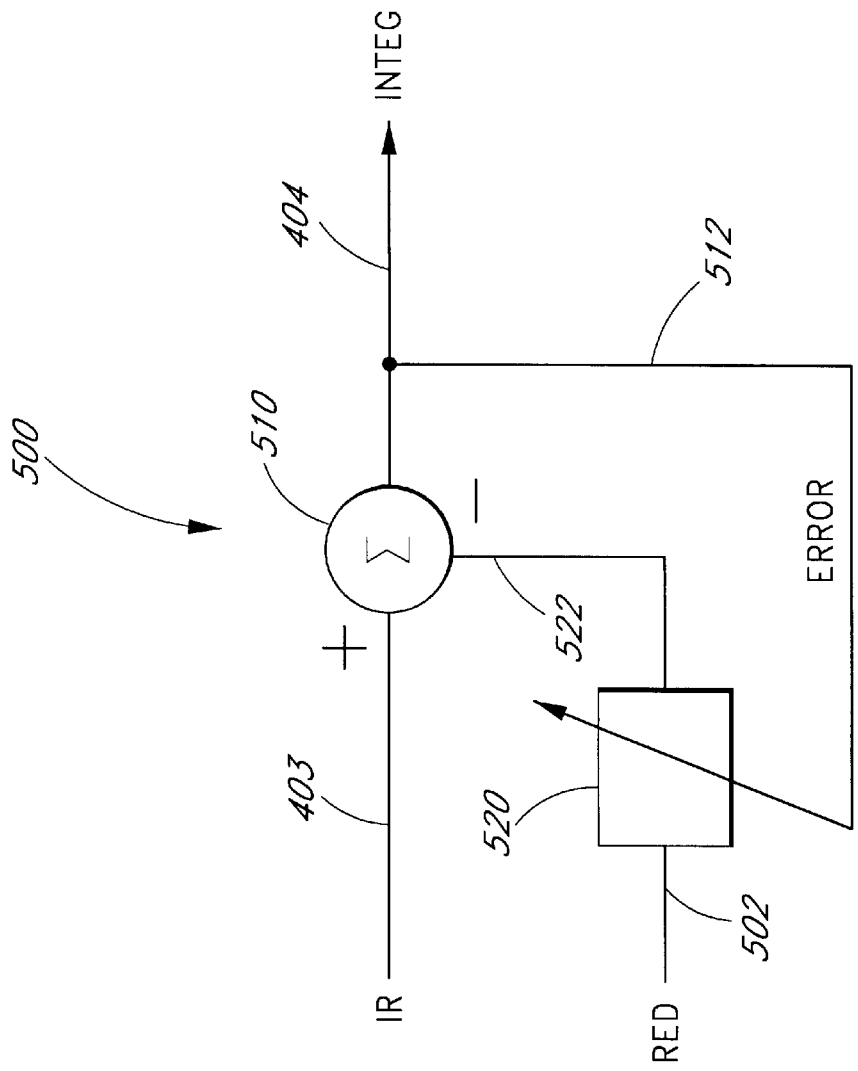

FIG. 5B illustrates the adaptive noise canceller 500. The reference input 502 is processed by an adaptive filter 520 that automatically adjusts its own impulse response through a least-squares algorithm. The least-squares algorithm responds to an error signal 512 that is the difference 510 between the noise canceller input 403 and the adaptive filter output 522. The adaptive filter is adjusted through the algorithm to minimize the power at the noise canceller output 404. If the IR 403 and Red 502 signals are relatively well-behaved with respect to the theoretical model for these signals, then the noise canceller output 404 will be relatively small. This model assumes that the same frequencies are present in the signal and noise portions of the IR and Red signals. By contrast, if a phenomenon such as scattering, hardware noise, or sensor decoupling, to name a few, affects one input signal differently than the other, then the power at the noise canceller output will be relatively large. More detail about the input signal model and the adaptive noise canceller 500 is given in U.S. Pat. No. 5,632,272 entitled "Signal Processing Apparatus," issued May 27, 1997, assigned to the assignee of the current application and incorporated by reference herein.

The PR density input 405 is a ratio of the sum of the periods of recognizable pulses within a waveform segment divided by the length of the waveform segment. This parameter represents the fraction of the waveform segment that can be classified as having physiologically acceptable pulses. In one embodiment, a segment represents a snapshot of 400 samples of a filtered input waveform, or a 6.4 second "snapshot" of the IR waveform at a 62.5 Hz sampling rate. The derivation of PR density is described in U.S. Pat. No. 6,464,311 entitled "Plethysmograph Pulse Recognition Processor," and cited above.

Other inputs to the pulse indicator 400 are the IR input 403, patient type 406 and reset 408. The IR input 403 is the detected IR signal preprocessed by taking the natural logarithm, bandpass filtering and scaling in order to normalize the signal and remove the direct current component, as is well known in the art. Patient type 406 is a Boolean value that indicates either an adult sensor or a neonate sensor is in use. Reset 408 initializes the state of the pulse indicator 400 to known values upon power-up and during periods of recalibration, such as when a new sensor is attached or a patient cable is reconnected.

Figure 6:
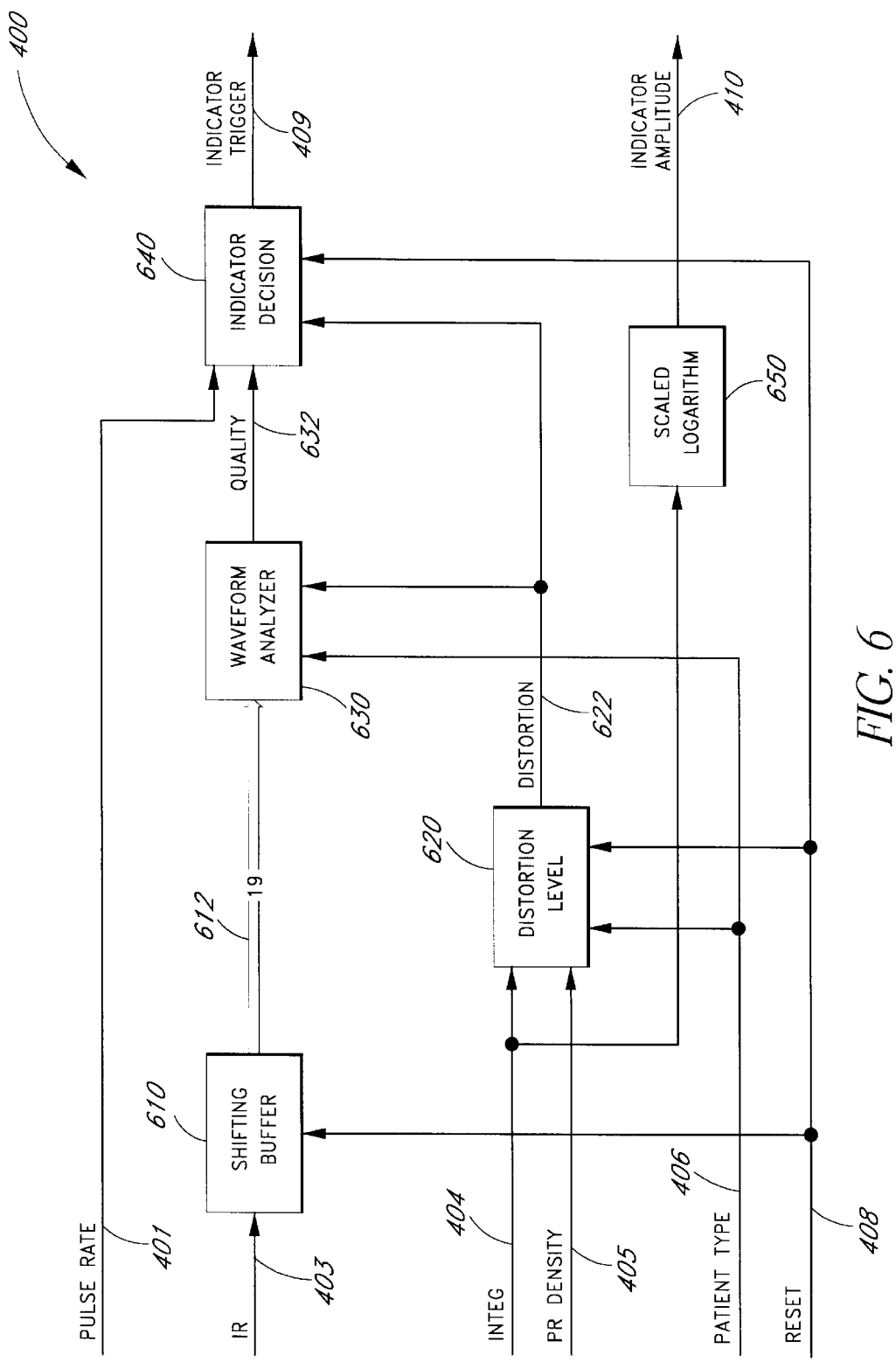
FIG. 6 is a top-level block diagram of the pulse indicator.

FIG. 6 is a functional block diagram of the pulse indicator 400. The pulse indicator 400 includes a shifting buffer 610, a distortion level function 620, a waveform analyzer 630, and a indicator decision 640, which together produce the indicator trigger 409. The pulse indicator 400 also includes a scaled logarithm function 650 that produces the indicator amplitude output 410. The shifting buffer 610 accepts the IR input 403 and provides a vector output 612 representing a fixed-size segment of the patient's plethysmograph input to the waveform analyzer 630. In a particular embodiment, the output vector is a 19 sample segment of the IR input 403. This waveform segment size represents a tradeoff between reducing the delay from pulse occurrence to pulse indicator, which is equal to 0.304 seconds at the 62.5 Hz input sample rate, yet providing a sufficiently large waveform segment to analyze. This fixed-sized segment is updated with each new input sample, and a new vector is provided to the waveform analyzer 630 accordingly.

The distortion level function 620 determines the amount of distortion present in the IR input signal 403. The inputs to the distortion level function 620 are the Integ input 404 and the PR density input 405. The distortion output 622 is a Boolean value that is "true" when distortion in the IR input 403 is above a predetermined threshold. The distortion output 622 is input to the waveform analyzer 630 and the indicator decision 640. The distortion output 622 determines the thresholds for the waveform analyzer 630, as described below. The distortion output 622 also affects the window size within which a pulse indication can occur, also described below. The distortion output 622 is also a function of the patient type input 406, which indicates whether the patient is an adult or a neonate. The reason for this dependence is also described below.

The waveform analyzer 630 determines whether a particular portion of the IR input 403 is an acceptable place for a pulse indication. The input to the waveform analyzer 630 is the vector output 612 from the shifting buffer 610, creating a waveform segment. A waveform segment portion meets the acceptance criteria for a pulse when it satisfies one of three conditions. These conditions are a sharp downward edge, a peak in the middle with symmetry with respect to the peak, and a peak in the middle with a gradual decline. If one of these criteria is met, the waveform analyzer "quality" output 632 is "true." Different criteria are applied depending on the state of the distortion output 622, which is also a waveform analyzer input. If the distortion output 622 indicates no distortion, strict criteria are applied to the waveform shape. If the distortion output 622 indicates distortion, looser criteria are applied to the waveform shape. Different criteria are also applied for waveforms obtained from adult and neonate patients, as indicated by the patient type 406. The specific criteria are described in further detail below.

The indicator decision 640 determines whether to trigger a pulse indication at a particular sample point of the input waveform. Specifically, the indicator decision 640 determines if it is the right place to trigger a pulse indication on the input waveform and if the time from the last pulse indication was long enough so that it is the right time to trigger another pulse indication. The decision as to the right place to trigger a pulse indication is a function of the analyzer output 632, which is one input to the indicator decision 640. The decision as to the right time for an indicator trigger is a function of the state of the distortion output 622, which is another input to the indicator decision 640. If the distortion output 622 is "false", i.e. no distortion is detected in the input waveform, then a fixed minimum time gap from the last indicator must occur. In a particular embodiment, this minimum time gap is 10 samples. If the distortion output 622 is "true", i.e. distortion is detected in the input waveform, then the minimum time gap is a function of the pulse rate input 401. This pulse rate dependent threshold is described in further detail below.

Figure 7:
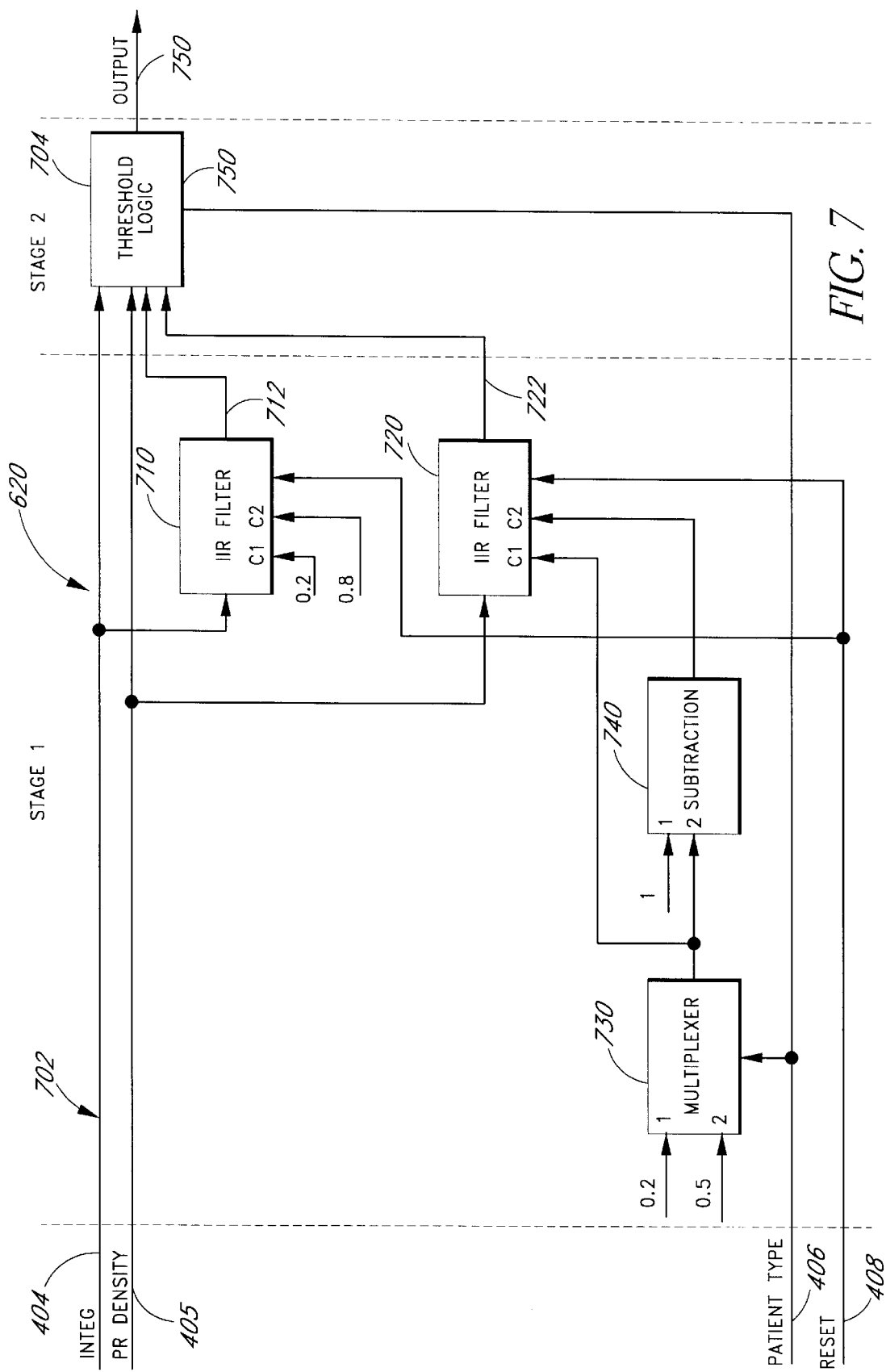
FIG. 7 is a detailed block diagram of the "distortion level" portion of the pulse indicator.

FIG. 7 is a detailed block diagram of the distortion level function 620. The distortion level function has two stages. The first stage 702 filters the Integ and PR density inputs. The second stage 704 decides whether distortion is present based on both the filtered and the unfiltered Integ input 404 and PR density 405 inputs. The first stage components are a first infinite impulse response (IIR) filter 710 for the Integ input 404 and a second IIR filter 720 for the PR density input 405.

Figure 8:
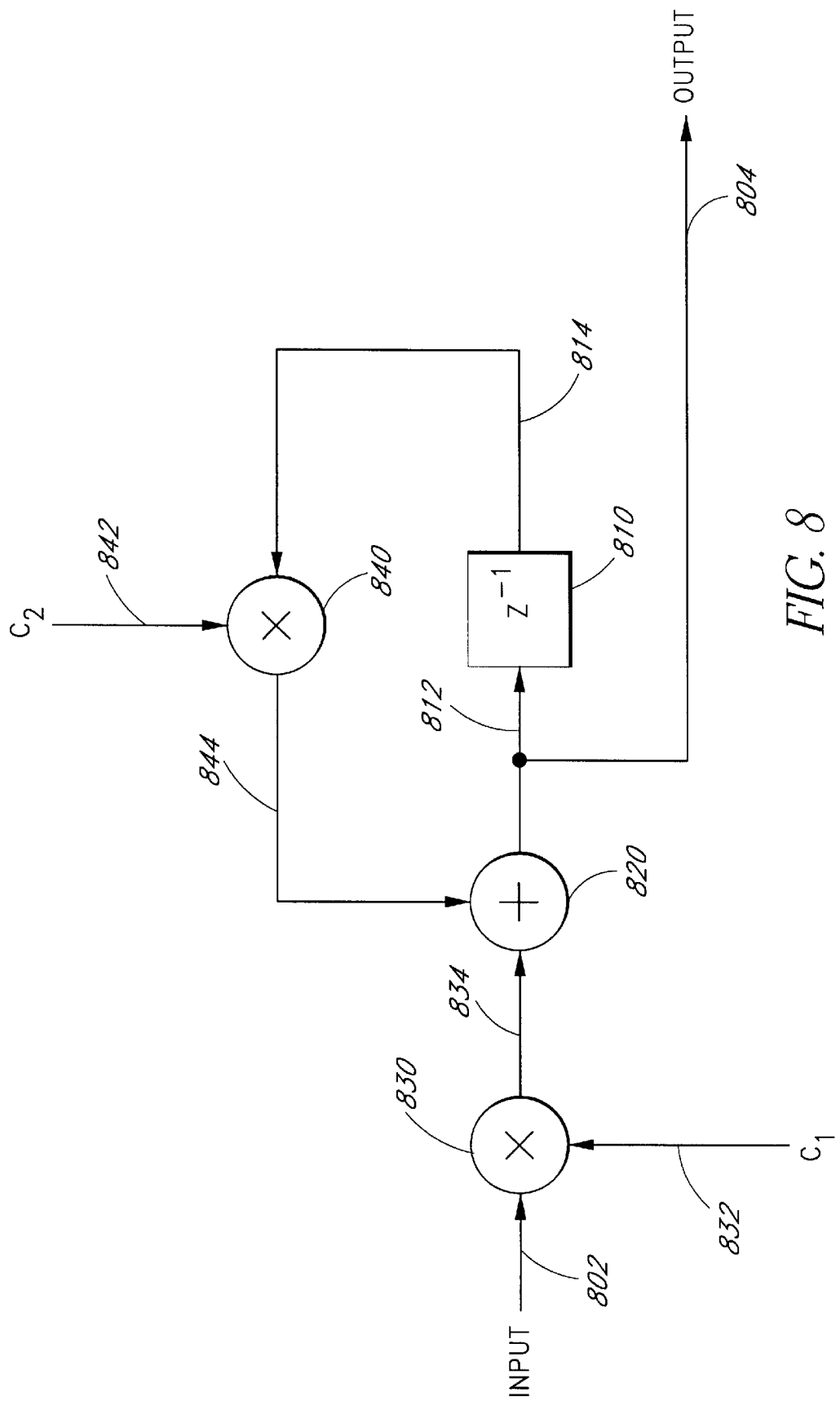
FIG. 8 is a block diagram of the infinite impulse response (IIR) filters of the "distortion level" portion illustrated in FIG. 7.

FIG. 8 illustrates the structure of the IIR filter 710, 720 (FIG. 7). Each of these filters has a delay element 810, which provides a one sample delay from the delay element input 812 to the delay element output 814. An adder 820 that sums a weighted input value 834 and a weighted feedback value 844 provides the delay element input 812. A first multiplier 830 generates the weighted input value 834 from the product of the input 802 and a first constant 832, $c_1$. A second multiplier 840 generates the weighted feedback value 844 from the product of the delay element output 814 and a second constant 842, $c_2$. With this structure, the filter output 804 is:

$$\text{Output}_n = c_1 \cdot \text{Input}_n + c_2 \cdot \text{Output}_{n-1} \quad (1)$$

That is, the nth output 804 is the weighted average of the input and the previous output, the amount of averaging being determined by the relative values of $c_1$ and $c_2$.

As shown in FIG. 7, the two IIR filters 710, 720 each apply different relative weights to the input signal. In one embodiment, the weights are fixed for the Integ filter 710 and are a function of the patient type for the PR density filter 720. In particular, for the Integ filter 710, $c_1=0.2$ and $c_2=0.8$. For the PR density filter 720, the combination of a multiplexer 730 and subtraction 740 set the values of $c_1$ and $c_2$ as a function of the patient type 406. If the signal is from an adult, then $c_1=0.2$ and $c_2=0.8$. If the signal is from a neonate, then $c_1=0.5$, $c_2=0.5$. Because a neonate pulse rate is typically higher than an adult, the PR density changes less quickly and, hence, less filtering is applied.

FIG. 7 also shows the second stage 704, which has threshold logic 750 for determining the presence of distortion. The inputs to the threshold logic 750 are Integ 404, PR density 405, filtered Integ 712 and filtered PR density 722. The threshold logic 750 is also dependent on the patient type 406. The distortion output 622 is a Boolean value that is "true" if distortion is present and "false" if no distortion is present. In one embodiment, the distortion output 622 is calculated as follows:

Adults $$\text{distortion output} = (\text{Integ} > 0.01) + (\text{filtered Integ} > 0.0001) \cdot (\text{filtered PR density} < 0.7) \quad (2)$$

Neonates $$\text{distortion output} = (\text{Integ} > 0.05) + ((\text{filter Integ} > 0.005) + (\text{PR density} = 0) \cdot (\text{filtered PR density} < 0.8) \quad (3)$$

where a logical "and" is designated as a multiplication "·" and a logical "inclusive or" is designated as an addition "+."

Figure 9:
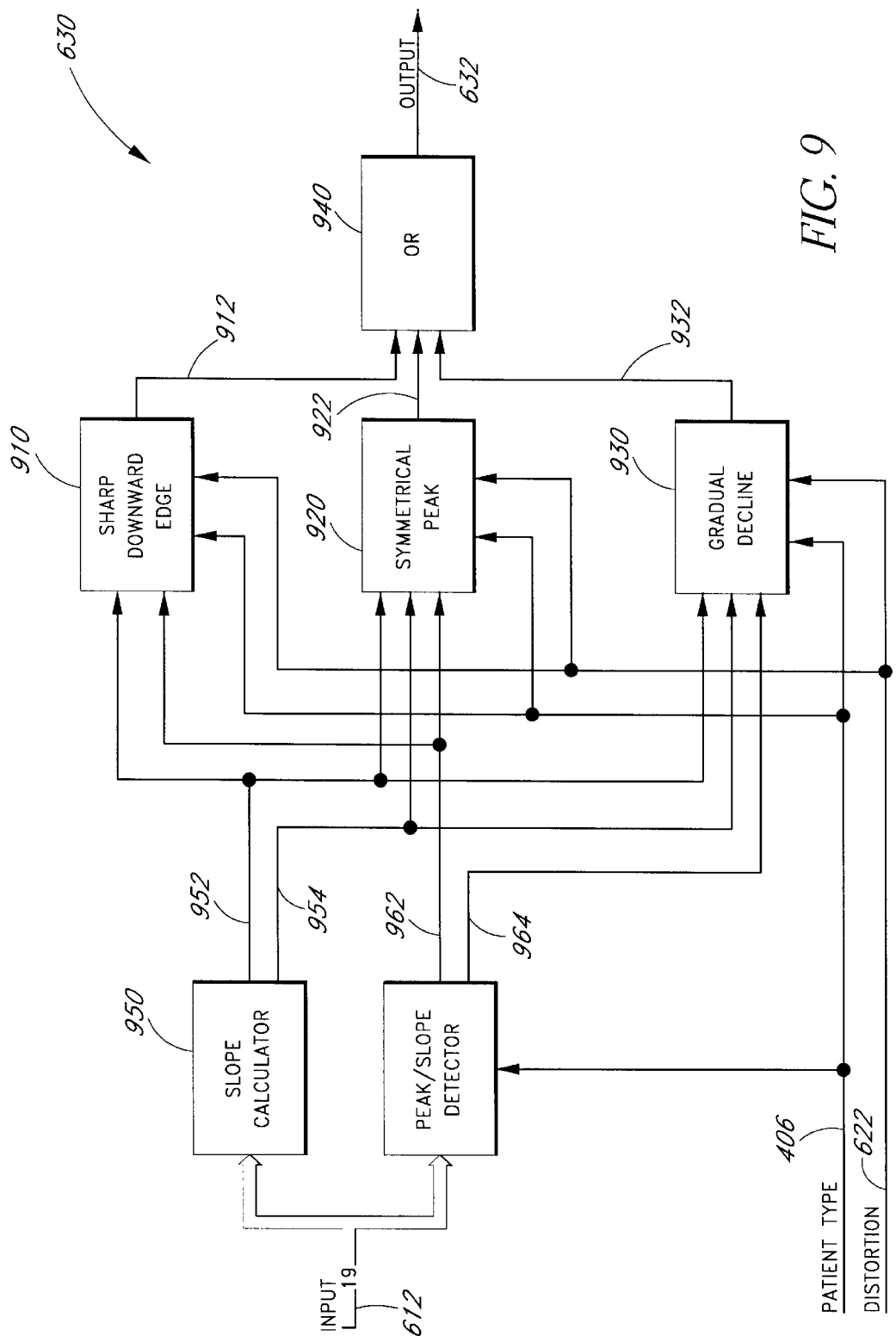
FIG. 9 is a detailed block diagram of the "waveform analyzer" portion of the pulse indicator.

FIG. 9 is a detailed block diagram of the waveform analyzer 630. As described above, the waveform analyzer 630 is based on three shape criteria, which are implemented with a sharp downward edge detector 910, a symmetrical peak detector 920 and a gradual decline detector 930. An "or" function 940 generates a waveform analyzer output 632, which has a "true" value if any of these criteria are met. The inputs to the waveform analyzer 630 are the IR waveform samples 612 from the buffer 610 (FIG. 6), patient type 406, and distortion 622 output from the distortion level function 620 (FIG. 6). The IR waveform samples 612 are a 19 sample vector representing a plethysmograph waveform segment. A slope calculator 950 and a peak/slope detector 960 provide inputs to the shape criteria components 910, 920, 930.

Figure 10:
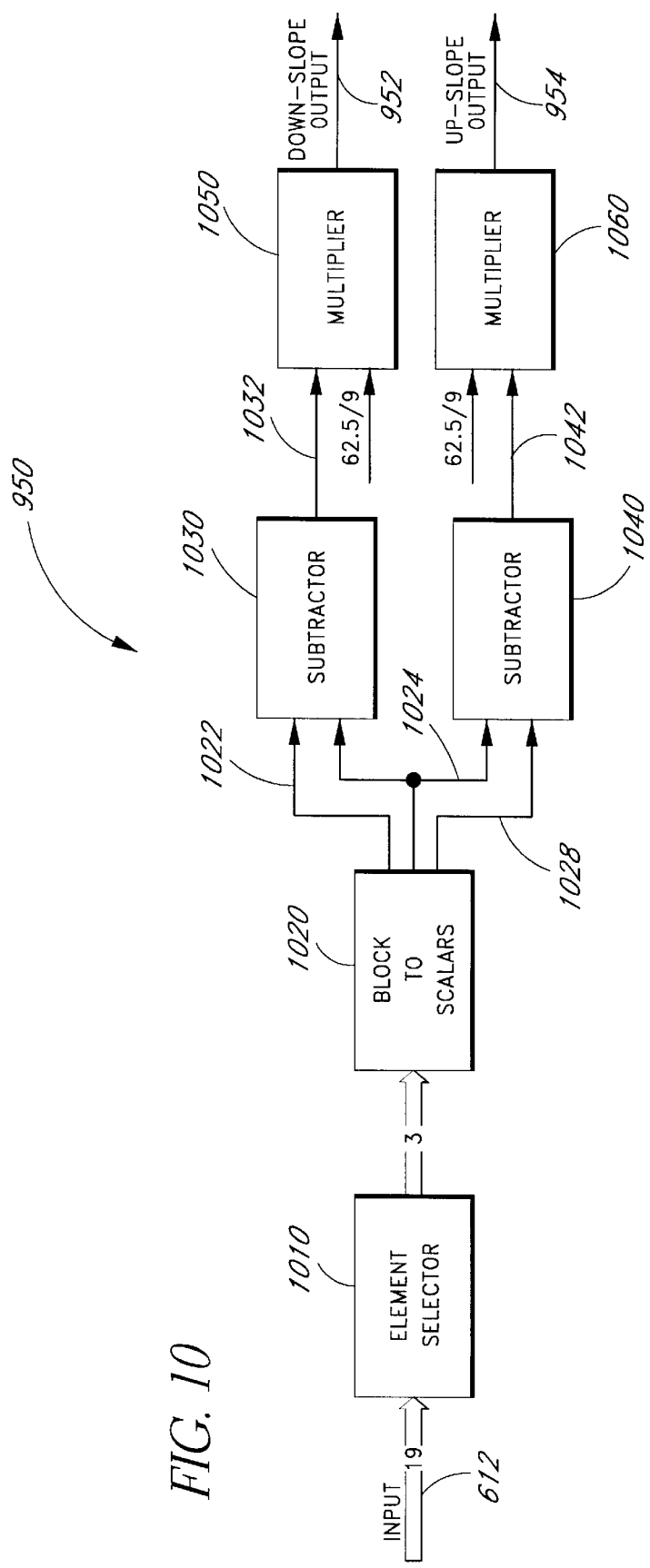
FIG. 10 is a detailed block diagram of the "slope calculator" portion of the waveform analyzer illustrated in FIG. 9.

Shown in FIG. 10, the slope calculator 950 operates on the IR waveform samples 612 to calculate a down slope value, which is provided on a down slope output 952, and an up slope value, which is provided on an up slope output 954. The down slope and up slope values are defined to be, respectively, the difference between the middle point and the last and first points, scaled by a factor of 62.5/9. The scaling factor is the sampling rate, 62.5 Hz, divided by the number of samples, 9, between the middle point and end point in the 19 sample IR waveform 612. The slope calculator 950 has an element selector 1010 that determines the center sample, the extreme left sample and the extreme right sample from the IR waveform 612. The block-to-scalars function 1020 provides a left sample output 1022 and a center sample output 1024 to a first subtractor 1030 and the center sample output 1024 and a right sample output 1028 to a second subtractor 1040. The first subtractor output 1032, which is the center value minus the right sample value, is scaled by 62.5/9 by a first multiplier 1050 that generates the down slope output 952. The second subtractor output 1042, which is the center value minus the left sample value, is scaled by 62.5/9 by a second multiplier 1060 that generates the up slope output 954.

Shown in FIG. 9, the peak/slope detector 960, like the slope calculator 950 has the IR waveform samples 612 as an input. The peak/slope detector 960 has two Boolean outputs, a peak output 962 and a slope output 964. The peak output 962 is "true" if the input waveform contains a peak. The slope output 964 is "true" if the input waveform contains a slope. The peak output 962 and slope output 964 are also dependent on the patient type 406 to the peak/slope detector 960. In one embodiment, the peak output 962 and slope output 964 are calculated as follows:

Adults $$\text{peak output} = (In_9 > 0) \Pi^3_{i=1}(In_7 - In_{7-i} > 0) \Pi^9_{i=3}(In_9 - In_{9+i} > -0.05) \quad (4)$$

$$\text{slope output} = (In_9 > 0) \Pi^{18}_{i=3}(In_{i-1} - In_i > -0.005) \quad (5)$$

Neonates $$\text{peak output} = \Pi^3_{i=1}(In_7 - In_{7-i} > 0) \Pi^9_{i=3}(In_9 - In_{9+i} > -0.05) \quad (6)$$

$$\text{slope output} = \Pi^{18}_{i=3}(In_{i-1} - In_i > -0.005) \quad (7)$$

where $In_i$ is the ith waveform sample in the 19 sample IR waveform 612.

FIG. 9 shows the sharp downward edge detector 910, which is the sub-component of the waveform analyzer 630 that determines whether the shape of the input waveform segment meets the sharp downward edge criteria. To do this, the edge detector 910 determines whether the down slope value is bigger than a certain threshold and whether a peak is present. The edge detector 910 has as inputs the down slope output 952 from the slope calculator 950, the peak output 962 from the slope/peak detector 960, the distortion output 622 from the distortion level function 620 (FIG. 6) and the patient type 406. The edge detector output 912 is a Boolean value that is "true" when the waveform shape criteria is met. In one embodiment, the edge detector output 912 is calculated as follows:

Adults and No Distortion $$\text{edge output} = (\text{down slope output} > 3) \cdot \text{peak output} \quad (8)$$

Neonates and No Distortion $$\text{edge output} = (\text{down slope value} > 1) \cdot \text{peak output} \quad (9)$$

Distortion (Adults or Neonates)

$$\text{edge output} = (\text{down slope value} > 0.65) \cdot \text{peak output} \quad (10)$$

FIG. 9 also shows the symmetrical peak detector 920, which is the sub-component of the waveform analyzer 630 that determines whether the waveform contains a symmetrical peak. To do this, the symmetrical peak detector 920 checks whether the down slope and up slope values are bigger than a certain threshold, if the difference between their magnitudes is small, and if a peak is present. The symmetrical peak detector 920 has as inputs the down slope output 952 and the up slope output 954 from the slope calculator 950, the peak output 962 from the slope/peak detector 960, the distortion output 622 from the distortion level function 620 (FIG. 6) and the patient type 406. The symmetrical peak output 922 is a Boolean value that is "true" when the waveform shape criteria is met. In one embodiment, the symmetrical peak output 922 is defined as follows:

Adults $$\text{symmetrical peak output} = \text{false} \quad (11)$$

Neonates and No Distortion $$\text{symmetrical peak output} = (\text{down slope} > 1) \cdot (\text{up slope} > 1) \cdot (|\text{down slope} - \text{up slope}| \leq 0.5) \cdot \text{peak} \quad (12)$$

Neonates and Distortion $$\text{symmetrical peak output} = (\text{down slope} > 0.35) \cdot (\text{up slope} > 0.35) \cdot (|\text{down slope} - \text{up slope}| \leq 0.5) \cdot \text{peak} \quad (13)$$

FIG. 9 further shows the gradual decline detector 930, which is the sub-component of the waveform analyzer 630 that determines whether the waveform contains a gradual decline. To do this, the decline detector 930 checks whether the difference between the down slope and the up slope values is in between two thresholds and if a slope is present. The decline detector 930 has as inputs the down slope output 952 and the up slope output 954 from the slope calculator 950, the slope output 964 from the slope/peak detector 960, the distortion output 622 from the distortion level function 620 (FIG. 6) and the patient type 406. The decline output 932 is a Boolean value that is "true" when the waveform shape criteria is met. In one embodiment, the decline output 932 is defined as follows:

Adults and No Distortion $$\text{decline} = (3 < (\text{down slope} - \text{up slope}) < 6) \cdot \text{slope} \quad (14)$$

Neonates and No Distortion $$\text{decline} = (0.5 < (\text{down slope} - \text{up slope}) < 2) \cdot \text{slope} \quad (15)$$

Distortion (Adults or Neonates)

$$\text{decline} = (0.5 < (\text{down slope} - \text{up slope}) < 8) \cdot \text{slope} \quad (16)$$

Figure 11:
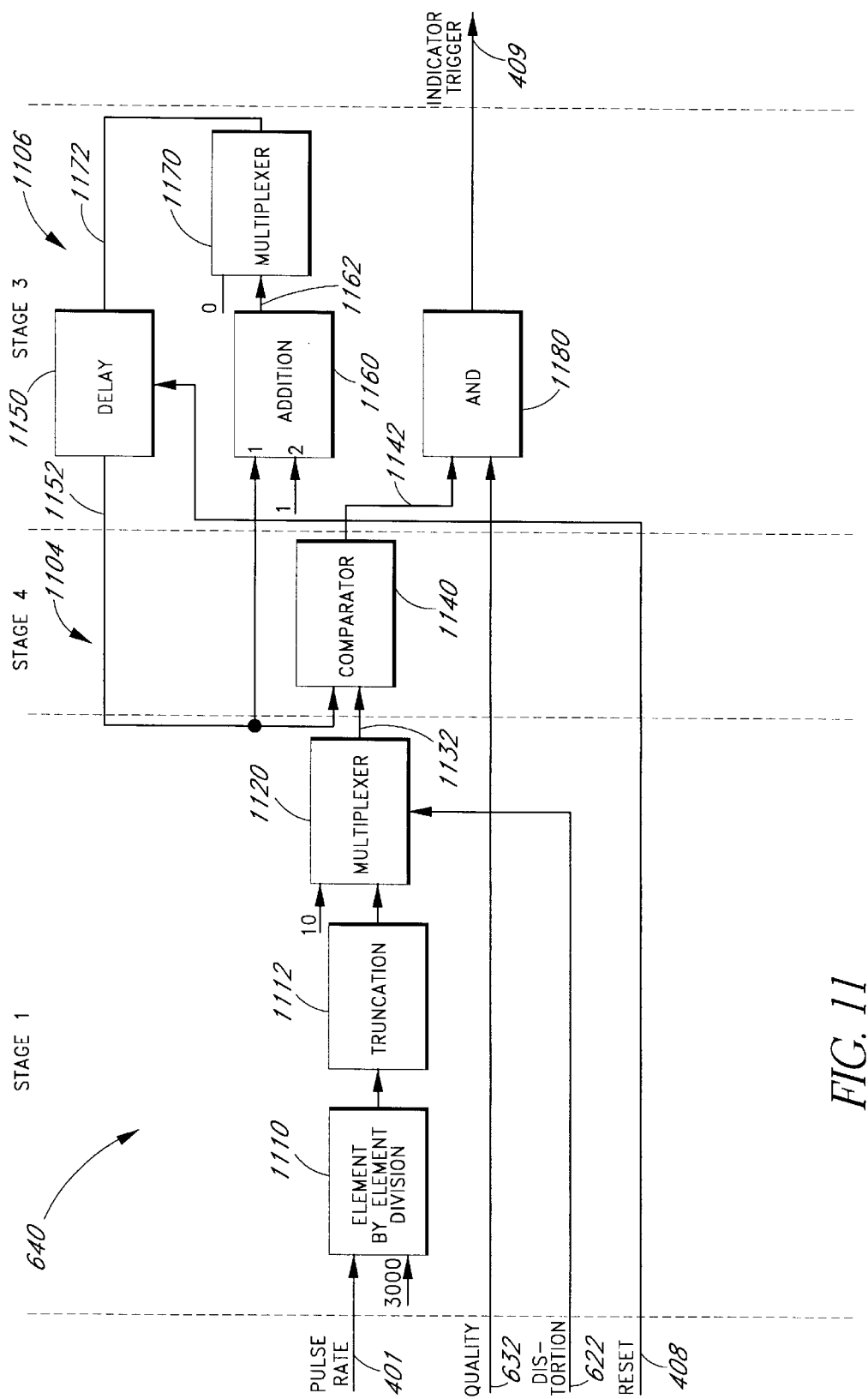
FIG. 11 is a detailed block diagram of the "indicator decision" portion of the pulse indicator.

FIG. 11 is a detailed block diagram of the indicator decision 640 sub-component. The first stage 1102 of the indicator decision 640 determines a minimum time gap after which a pulse indicator can occur. The second stage 1104 determines whether the number of samples since the last indicator is greater than the minimum allowed pulse gap. The third stage 1106 decides whether to generate a pulse indicator trigger. If no trigger occurs, a sample count is incremented. If an indicator trigger occurs, the sample count is reset to zero.

As shown in FIG. 11, the first stage 1102 has a divider 1110, a truncation 1120 and a first multiplexer 1130. These components function to set the minimum allowable gap between pulse indications. Under no distortion, the minimum gap is 10 samples. Under distortion, the gap is determined by the pulse rate. Specifically, under distortion, the minimum gap is set at 80% of the number of samples between pulses as determined by the pulse rate input 401. This is computed as 0.8 times the sample frequency, 62.5 Hz., divided by the pulse rate in pulses per second, or:

$$\text{min. gap} = 0.8 \times (60/\text{pulse rate}) \times 62.5 = 3000/\text{pulse rate} \quad (17)$$

The divider 1110 computes 3000/pulse rate. The divider output 1112 is truncated 1120 to an integer value. The first multiplexer 1130 selects the minimum gap as either 10 samples if the distortion input 622 is "false" or the truncated value of 3000/pulse rate if the distortion input 622 is "true." The selected value is provided on the multiplexer output 1132, which is fed to the second stage 1104. The second stage 1104 is a comparator 1140, which provides a Boolean output 1142 that is "true" if a counter output 1152 has a value that is equal to or greater than the minimum gap value provided at the first multiplexer output 1132.

FIG. 11 also illustrates the third stage 1106, which has a counter and an "and" function. The counter comprises a delay element 1150 providing the counter output 1152, an adder 1160 and a second multiplexer 1170. When the counter is initialized, the second multiplexer 1170 provides a zero value on the multiplexer output 1172. The multiplexer output 1172 is input to the delay element, which delays the multiplexer output value by one sample period before providing this value at the counter output 1152. The counter output 1152 is incremented by one by the adder 1160. The adder output 1162 is input to the second multiplexer 1162, which selects the adder output 1162 as the multiplexer output 1172 except when the counter is initialized, as described above. The counter is initialized to zero when the pulse indicator trigger 409 is "true" as determined by the output of the "and" element 1180. The "and" 1180 generates a "true" output only when the comparator output 1142 is "true" and the quality output 632 from the waveform analyzer 630 (FIG. 6) is also "true."

Figure 12:
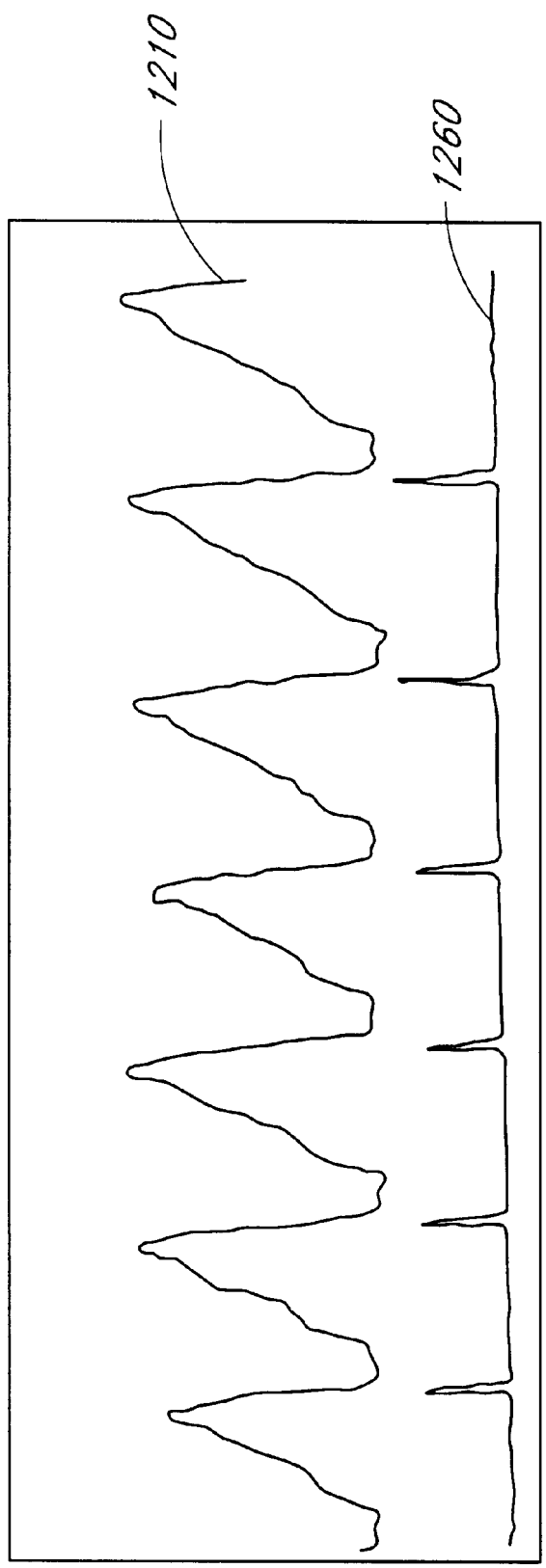
FIG. 12 is a display illustrating a normal plethysmograph and a corresponding visual pulse indicator.
Figure 13:
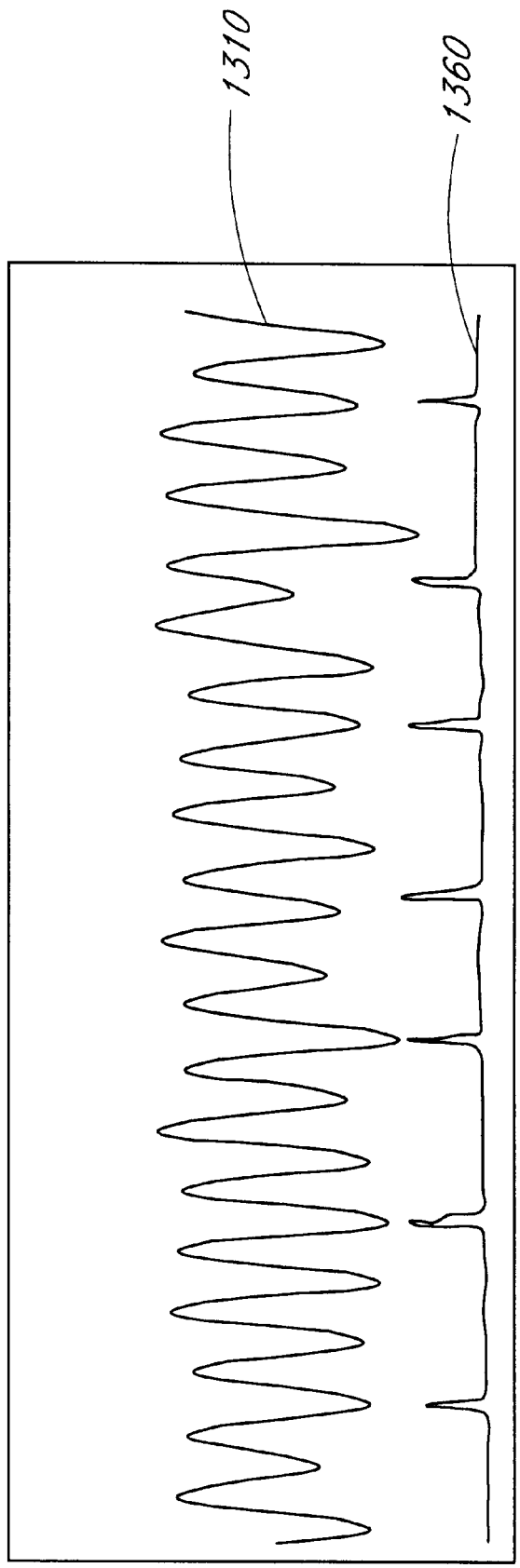
FIG. 13 is a display illustrating a distorted plethysmograph and a corresponding high-confidence-level visual pulse indicator.
Figure 14:
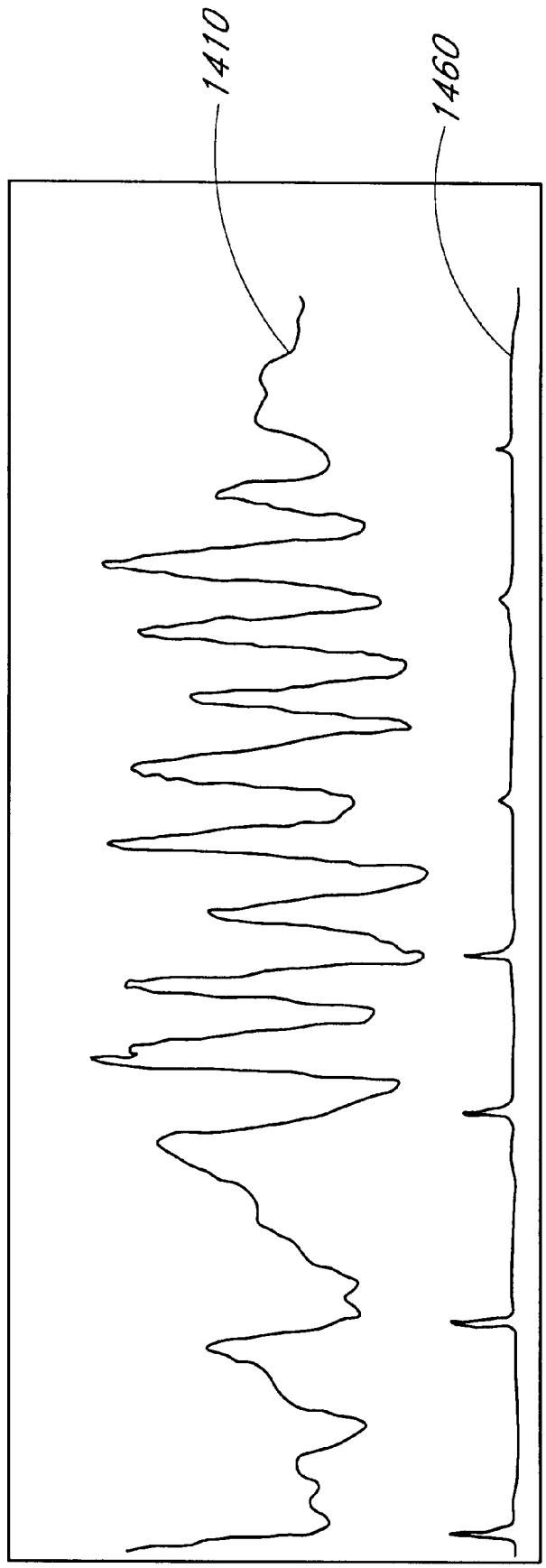
FIG. 14 is a display illustrating a distorted plethysmograph and a corresponding low-confidence-level visual pulse indicator.

FIGS. 12–14 illustrate a visual pulse indicator generated in response to the indicator trigger output 409 (FIG. 4) and indicator amplitude output 410 of the pulse indicator 400 (FIG. 4). In FIG. 12, the top trace 1210 is an exemplar plethysmograph waveform without significant distortion. The bottom trace 1260 is a corresponding visual pulse indication comprising a series of relatively large amplitude spikes that are generally synchronous to the falling edges of the input waveform 1210. Because the input waveform 1210 has low distortion, the pulse indication 1260 is somewhat redundant, i.e. pulse occurrence and data confidence is apparent from the input waveform alone. Nevertheless, FIG. 12 illustrates the visual pulse indicator according to the present invention.

In FIG. 13, the plethysmograph waveform illustrated in the top trace 1330 displays significant distortion. In contrast to the example of FIG. 12, pulse occurrence and data confidence is not obvious from the input waveform alone. The corresponding visual pulse indicator 1360, however, indicates pulse occurrence at the location of the display spikes. Further, the relatively large spike amplitude indicates high data integrity and a corresponding high confidence in the computed values of pulse rate and saturation despite the waveform distortion.

In FIG. 14, the plethysmograph waveform 1410 also displays significant distortion. In contrast to the example of FIG. 13, the visual pulse indicator 1460 displays relatively low amplitude spikes corresponding to the latter half of the waveform sample, indicating relatively low data integrity and low confidence in the computed pulse rate and saturation.

The pulse oximetry pulse indicator has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A processing apparatus having as an input a plethysmograph waveform, said waveform comprising a plurality of pulses, said apparatus generating a trigger synchronous with the occurrence of said pulses, said apparatus comprising:

a waveform analyzer in communication with said waveform and responsive to the shape of said pulses, wherein the waveform analyzer derives a measure of distortion in said waveform that is indicative of a quality of said waveform; and a decision element conditionally responsive to said measure of distortion derived by said waveform analyzer to provide said trigger.

2. The processing apparatus of claim 1 further comprising a pulse rate input, wherein said decision element is conditionally responsive to said pulse rate input to provide said trigger.

3. The processing apparatus of claim 2 wherein said decision element is responsive to said measure of distortion when said measure of distortion indicates that said waveform is substantially undistorted and is responsive to said pulse rate when said waveform is substantially distorted.

4. The processing apparatus of claim 1 wherein said trigger is used to generate an audible indicator of pulse occurrence.

5. The processing apparatus of claim 1 wherein said trigger is used to generate a visual indicator of pulse occurrence.

6. The processing apparatus of claim 5 wherein said visual indicator also incorporates an indication of data integrity.

7. A method of indicating a pulse in a plethysmograph waveform comprising the steps of:

deriving a measure of distortion in said waveform; wherein said measure of distortion is indicative of a quality of said waveform;

establishing a trigger criterion dependent on said measure;

determining whether said trigger criterion is satisfied to provide a trigger; and generating a pulse indication upon occurrence of said trigger.

8. The method of claim 7 wherein said deriving step comprises the steps of:

computing a first value related to integrity of said waveform;

computing a second value related to the recognizable pulses in said waveform; and combining said first value and said second value to derive said measure.

9. The method of claim 7 wherein said trigger criterion is based on a waveform shape.

10. The method of claim 7 wherein said trigger criterion is based on a pulse rate.

11. An apparatus for indicating the occurrence of pulses in a plethysmograph waveform comprising:

a waveform analyzer means for recognizing a physiological pulse in said waveform;

a detector means for determining a measure of distortion in said waveform, wherein said measure of distortion is indicative of a quality of said waveform;

a decision means for triggering a pulse indicator based on at least one of said physiological pulse and a pulse rate depending on said measure.

* * * * *